United States Patent [19]

Shaw et al.

[11] 4,301,031

[45] Nov. 17, 1981

[54] METHACROLEIN OXIDATION CATALYSTS

[75] Inventors: Wilfrid G. Shaw, Lyndhurst; Philip L. Kuch, Aurora; Christos Paparizos, Willowick, all of, OH

[73] Assignee: The Standard Oil Company, Cleveland, Ohio

[21] Appl. No.: 175,236

[22] Filed: Aug. 5, 1980

[51] Int. Cl.³ .............................................. B01J 27/14
[52] U.S. Cl. ...................................... 252/435; 252/437
[58] Field of Search ................................ 252/435, 437

[56] References Cited

U.S. PATENT DOCUMENTS

| | | | |
|---|---|---|---|
| 3,976,688 | 8/1976 | Akiyamo et al. | 252/437 |
| 4,017,423 | 4/1977 | White et al. | 252/437 |
| 4,042,533 | 8/1977 | Shaw et al. | 252/437 |
| 4,101,448 | 7/1978 | Shaw et al. | 252/437 |
| 4,166,190 | 8/1979 | White et al. | 252/437 X |
| 4,174,459 | 11/1979 | Sakamoto et al. | 252/435 X |
| 4,225,466 | 9/1980 | Wada et al. | 252/435 |

FOREIGN PATENT DOCUMENTS 1482686  8/1977  United Kingdom .

*Primary Examiner*—Delbert E. Gantz
*Assistant Examiner*—William G. Wright
*Attorney, Agent, or Firm*—Salvatore P. Pace; Herbert D. Knudsen; Larry W. Evans

[57] ABSTRACT

Compositions of the empirical formula:

$$Mo_{12}P_{0.1-3}M_{0.1-3}Cu_{0.1-2}V_{0.1-2}X_{0.01-2}Y_aO_b \quad (I)$$

where
 M is at least one of K, Rb and Cs;
 X is at least one of Ba, La, Ga, Al, Ag, Cd, Ti, Tl, Hg, Pb and Zn;
 Y is at least one of Fe, Co, Ni, Sr, Mn, In, Ta, Ge, S and Be when $a>0$;
 a is a number of 0 to about 2; and
 b is a number that satisfies the valence requirements of the other elements present, are excellent catalysts for the oxidation of methacrolein to methacrylic acid.

14 Claims, No Drawings

METHACROLEIN OXIDATION CATALYSTS

BACKGROUND OF THE INVENTION

1. Field of the Invention

This invention relates to catalysis. In one aspect, the invention relates to novel phosphomolybdic acid catalysts while in another aspect, the invention relates to the use of these catalysts in the oxidation of methacrolein to methacrylic acid.

2. Description of the Prior Art

The art is replete with various phosphomolybdic acid catalysts useful for the oxidation of acrolein to acrylic acid. Illustrative of this art are U.S. Pat. Nos. 4,101,448, 4,115,441, 4,042,533, 4,166,190 and 3,976,688. However, many of these catalysts contain tungsten and many, if not most, whether they contain tungsten or not, are not suitable for the commercial production of methacrolein to methacrylic acid. Of those catalysts that are suitable, none are entirely so. All are subject to improvement in methacrylic acid selectivity and thermal stability. Examples of catalysts now taught to be suitable for methacrolein oxidation include Belgium Pat. No. 823,897, Great Britian Pat. No. 1,482,686, U.S. Pat. No. 3,976,688 and U.S. Pat. No. 4,017,423. The Belgium patent teaches a phosphomolybdic acid catalyst that can be combined with any number of optional components; the British patent teaches a P-Mo-Cu-V-W catalyst that can also be combined with optional components; U.S. Pat. No. 3,976,688 teaches a catalyst similar to the phosphomolybdic acid catalyst of the Belgium patent but containing rubidium, cesium or potassium; and U.S. Pat. No. 4,017,423 teaches a promoted Rb-Mo-P catalyst.

SUMMARY OF THE INVENTION

According to this invention, compositions of the empirical formula:

$$Mo_{12}P_{0.1-3}M_{0.1-3}Cu_{0.1-2}V_{0.1-2}X_{0.01-2}Y_aO_b \qquad (I)$$

where
M is at least one of K, Rb and Cs;
X is at least one of Ba, La, Ga, Al, Ag, Cd, Ti, Tl, Hg, Pb and Zn;
Y is at least one of Fe, Co, Ni, Sr, Mn, In, Ta, Ge, S and Be when a >0;
a is a number of 0 to about 2; and
b is a number that satisfies the valence requirements of the other elements present
are excellent catalysts for the oxidation of methacrolein to methacrylic acid. These catalysts demonstrate both excellent selectivity for methacrylic acid and excellent thermal stability.

DETAILED DESCRIPTION OF THE INVENTION

Catalysts

The catalytic compositions of this invention, as evidenced from formula I, comprise at least seven elements, i.e. molybdenum, phosphorus, alkali metal (M), copper, vanadium, oxygen and at least one metal X all present in designated, proportional amounts. Preferably, the subscript value of phosphorus in formula I is about 0.5 to 1.75, of alkali metal (M) about 0.8 to 2, of copper about 0.1 to 0.8, of vanadium about 0.1 to 0.8, and of X about 0.02 to 0.5. The exact structure or element arrangement of these catalysts are not known but the metal and phosphorus components are present in the form of their oxides, acids or oxide or oxyacid complexes. However, the compositions of formula I are known not to be a mere physical mixture of their components but rather unique heteropolyacids where the individual components are chemically and/or physically bonded to one another.

Preferred catalysts are those where X is barium, mercury, thallium, zinc or lead and most preferred catalysts are those where X is barium, mercury or lead. In these preferred catalysts, M is typically rubidium or potassium. These catalyts can be further enhanced, at least in terms of activity and, in some cases thermal stability, by the addition of yet another component, here designated Y. When component Y is present (a>0), it is generally as iron, cobalt, tantalum or germanium.

As is taught by formula I, certain of the components can be combinations of two or more elements, e.g. X can be a combination of barium and zinc. In such instances, the subscript value represents the sum of the elements (e.g. for X, the sum of barium and zinc is a number of about 0.01 to 2). Generally, M, X and Y each represent but a single element.

Particularly preferred catalytic compositions are seven element or component (including oxygen) catalyts where M is rubidium or potassium, X is barium, mercury or lead and a is zero.

The catalytic compositions of this invention can be used in either the 100% active form or in a diluted form, i.e. supported or unsupported. Suitable support materials include silica, titania, alumina, zirconia, silicon carbide, boron, various phosphates, etc. with low surface area (about 1 m²/g) alumina a preferred support material. If a support is used, the catalytic composition is generally present in an amount of at least about 20 weight percent, based upon the combined weight of the support and catalytic composition, and preferably in an amount of at least about 30 weight percent.

The catalytic compositions of this invention can be prepared in any of a number of different methods, the particular method employed being a matter of convenience. Typically, the catalysts are prepared by mixing the appropriate catalyst ingredients in the proper proportion in an aqueous mixture, drying the resulting aqueous slurry with or without a reducing agent, and subsequently calcining the product. The ingredients can be added in any order during the preparation procedure but certain orders are preferred, particularly the mixing of the metallic ingredients prior to the addition of phosphorus (generally in the form of phosphoric acid). The ingredients employed can be the oxides, halides, nitrates, acetates or other salts of the particular metals or element added, and particularly preferred is the use of water soluble salts of the metal components. If a support is used, the materials comprising the support may be incorporated into the catalyst along with other ingredients or the catalytic composition may be coated and/or impregnated onto or into a core. After the catalyst ingredients have been combined to form an aqueous slurry, the slurry is taken to dryness and the dried solid obtained is heated in the presence of air, nitrogen, nitric oxide or a mixture of any two or more of these gases at temperatures between about 300° and 420° C. This calcination can take place outside the catalytic reactor or an in situ activation can be utilized. Other methods of preparation are broadly taught in the art.

In another embodiment of this invention, the compositions of formula I are highly effective catalysts for the oxidation of methacrolein to methacrylic acid. These catalytic compositions are used in the same manner as known catalytic compositions. The oxidation of methacrolein is a known reaction involving generally the contact of gaseous methacrolein with molecular oxygen at an elevated temperature. This particular embodiment of the invention is the use of these novel catalytic compositions in combination with the parameters of the known art process.

Exemplary of this known process is the contacting of gaseous methacrolein with molecular oxygen in the presence of steam at a temperature between about 275° C. and 340° C. in the presence of a catalytic amount of catalyst. The ratio of the reactants can vary widely with mole ratios of molecular oxygen to aldehyde of about 1 to 5 being typical. The amount of steam can also vary widely from a small amount generated in the reaction to 20 or more moles of steam per mole of aldehyde. Preferably, about 1 to 10 moles of steam per mole of aldehyde is employed in the reactant feed. In certain embodiments of this invention, recycle gas (principally $N_2$, $O_2$, $CO_2$ and $CO$) can be used with or instead of steam. Molecular oxygen is most conveniently added as air.

The oxidation reaction may be conducted in a fixed-bed, fluid-bed or transfer line reactor using atmospheric, superatmospheric or subatmospheric pressure. The contact time of reactants over the catalysts can vary from a fraction of a second to 20 or more seconds, the exact time depending upon the reaction conditions, such as catalyst composition, feed composition, temperature, pressure, reactor, etc.

Although the catalytic compositions of this invention find particular usefulness in the oxidation of methacrolein to methacrylic acid, they also have usefulness in other oxidation reactions. For example, these catalytic compositions are useful in the oxidation of acrolein to acrylic acid.

The following examples are illustrative of certain specific embodiments of this invention. Unless otherwise indicated, all parts and percentages are by weight.

SPECIFIC EMBODIMENTS

Catalyst Preparation

The catalyst used in the following examples were prepared by dissolving with stirring, ammonium heptamolybdate in distilled water and heating the resulting solution to 30°-35° C. While continuously stirring and maintaining the temperature, an alkali metal hydroxide and the halide or hydroxide of the X component were added. After 15 min., copper acetate and ammonium metavanadate solutions were added followed by a hydrochloric acid solution. The resulting slurry was then heated to 70° C. for 2 hours. Subsequently, the halide or hydroxide of the Y component(s) was added followed by addition of phosphoric acid. Stirring and heating were then continued for about 30 min. followed by a pH adjustment to 5.6. The mixture was evaporated to a thick paste and then dried in an oven at 100°-120° C. The resulting powder was then coated onto ⅛ in. Alundum ® spheres (alumina) such that the coating constituted about 35 weight percent of the coated spheres.

Those catalysts not having a Y component were prepared in the same manner but the step of adding the Y component was eliminated.

Process Procedure and Conditions

The experiments were conducted in a 20 cc downward flow, fixed-bed reactor. All runs were performed in the same manner: one hour at 370° C. with air flow (no feed) followed by one hour at 345° C. with feed, followed by a temperature drop to the reaction temperature. After a short stabilization period, a run was conducted for 15 min. to obtain sufficient reactor effluent for analysis. Off-gas rate was measured with a soap-film meter and the off-gas composition was determined at the conclusion of each run with the aid of a Perkin-Elmer 154 gas chromatograph. At the end of each run the entire scrubber liquid was diluted with distilled water to about 100 g. A weighed amount of methanol was used as an internal standard in a 20 g aliquot of the diluted solution. A one microliter sample was analyzed in a Varion Model 3700 gas chromatograph fitted with a flame ionization detector and a Chromosorb 107 column, 60/80 mesh. Total amounts of organic acid were determined by titrating 25 cc of the liquid with 0.1 N sodium hydroxide. The splits between methacrylic, acrylic and acetic acid were determined by gas chromatographic analysis.

The process conditions were:
Pressure—atmospheric
Run Time—15 min
Contact Time—3.2 sec
Feed Ratio—methacrolein/water/air: 1/4/10.5
Temperature (° C.)—325
VVH[1]—35

[1]Volume of methacrolein pr volume of catalyst per hour.

The results of runs made with various catalysts are reported in Table I.

TABLE I

METHACROLEIN OXIDATION

| Example | Composition of the Coating | Temp (°C.) | MAA[1] | Methac Conv.[2] | Acetic Acid | CO+ CO$_2$ | MAA Select.[3] | Carbon Balance |
|---|---|---|---|---|---|---|---|---|
| A | Mo$_{12}$ P Rb Cu$_{.25}$V$_{.25}$O$_b$ | 326 | 72.4 | 89.7 | 4.2 | 12.0 | 80.8 | 99.2 |
| B | Mo$_{12}$ P Rb Cu$_{.25}$V$_{.25}$O$_b$ | 325 | 72.2 | 91.7 | 5.9 | 12.3 | 78.8 | 99.4 |
| 1 | Mo$_{12}$ P Rb Cu$_{.25}$V$_{.25}$Ba$_{.1}$ O$_b$ | 326 | 78.4 | 91.2 | — | 11.4 | 86.0 | 104.0 |
| 2 | Mo$_{12}$ P Rb Cu$_{.25}$V$_{.25}$Ba$_{.1}$ O$_b$ | 325 | 77.5 | 94.3 | 2.2 | 13.3 | 82.2 | 107.0 |
| 3 | Mo$_{12}$ P Rb Cu$_{.25}$V$_{.25}$Hg$_{.1}$ O$_b$ | 325 | 79.4 | 94.3 | 1.7 | 12.4 | 84.0 | 97.4 |
| 4 | Mo$_{12}$ P Rb Cu$_{.25}$V$_{.25}$Pb$_{.1}$ O$_b$ | 325 | 79.2 | 95.7 | 0.9 | 14.3 | 82.7 | 103.5 |
| 5 | Mo$_{12}$ P Rb Cu$_{.25}$V$_{.25}$Pb$_{.1}$ O$_b$ | 325 | 74.7 | 99.7 | 0.9 | 14.3 | 80.2 | 103.6 |
| 6 | Mo$_{12}$ P K Cu$_{.25}$V$_{.25}$Ba$_{.1}$ O$_b$ | 325 | 76.8 | 94.0 | 1.8 | 14.3 | 81.7 | 101.1 |
| 7 | Mo$_{12}$ P K Cu$_{.25}$V$_{.25}$Ba$_{.1}$ Ge$_{.1}$ O$_b$ | 325 | 77.4 | 95.2 | 2.2 | 14.6 | 81.3 | 101.0 |

[1]Methacrylic Acid Yield = Moles of Methacrylic Acid Recovered × 100/Moles of Methacrolein Fed
[2]Methacrolein Conversion = Moles of Methacrolein Reacted × 100/Moles of Methacrolein Fed
[3]Methacrylic Acid Selectivity = Methacrylic Acid Yield × 100/Methacrolein Conversion In comparative examples A and B, the catalyst did not contain a component X, e.g. barium, mercury or lead. Comparison of the methacrylic acid yield, methacrolein conversion and methacrylic acid selectively of comparative examples A and B with examples 1–7 clearly demonstrates the superior performance of the latter over the former.

Thermal Stability

The superior stability of the catalysts of this invention was demonstrated by measuring the decline in activity of two catalysts differing principally by the presence or absence of the component X, here barium. Both catalysts were exposed to a feed mixture similar to that used in examples 1–7 at 345° C. for an extended period of time. Periodic feed conversion measurements were taken as a gage of catalyst activity. The catalyst compositions and activity measurements are reported in Table II.

TABLE II

THERMAL STABILITY MEASUREMENTS

| Hours | % Total Conversion | % Methacrylic Acid | Selectivity |
|---|---|---|---|
| C. | $Mo_{12}P_{0.15}Rb\,V_{0.25}Cu_{0.25}O_b$ | | |
| 2.9 | 98.7 | 72.1 | 73.0 |
| 20.6 | 96.5 | 68.5 | 70.9 |
| 27.9 | 93.1 | 69.9 | 75.1 |
| 49.0 | 84.0 | 64.4 | 76.6 |
| 51.0 | 79.8 | 63.7 | 80.0 |
| 8. | $Mo_{12}P_{0.15}Rb\,V_{0.25}Cu_{0.25}Ba_{0.1}O_b$ | | |
| 2.0 | 97.9 | 76.0 | 77.7 |
| 19.0 | 98.8 | 75.9 | 76.9 |
| 26.0 | 98.8 | 76.1 | 77.1 |
| 44.3 | 98.2 | 76.3 | 77.7 |
| 67.2 | 97.1 | 79.0 | 81.3 |

The data of comparative example C indicates that the activity, as measured by the percent total conversion, fell from 98.7 after 2.9 hours to 79.8 after 51 hours. In contrast, the activity of the catalyst of example 8, the catalyst of this invention, had essentially the same rate after 67 hours as it had after 2 hours. Moreover, conversion to methacrylic acid and selectivity to methacrylic acid was higher for the catalyst of example 8 than for the catalyst of example C over the entire test period.

Although the invention has been described in considerable detail through the preceding examples, these examples are for the purpose of illustration only and it is understood that variations and modifications can be made by one skilled in the art without departing from the spirit and scope of the invention.

The claimed invention is:

1. A catalytic composition of the empirical formula:

$$Mo_{12}P_{0.1-3}M_{0.1-3}Cu_{0.1-2}V_{0.1-2}X_{0.01-2}Y_aO_b \qquad (I)$$

where

M is at least one of K, Rb and Cs;

X is at least one of Ba, La, Ga, Al, Ag, Cd, Ti, Tl, Hg, Pb and Zn;

Y is at least one of Fe, Co, Ni, Sr, Mn, In, Ta, Ge, S and Be when a≧0;

a is a number of 0 to about 2; and b is a number that satisfies the valence requirements of the other elements present 2. The composition of claim 1 wherein M is potassium or rubidium.

3. The composition of claim 2 where X is barium, mercury, thallium, lead or zinc.

4. The composition of claim 2 where X is barium, mercury or lead.

5. The composition of claim 4 where a is 0.

6. The composition of claim 4 where a>0.

7. The composition of claim 6 where Y is iron, cobalt, tantalum or germanium.

8. The composition of claim 7 wherein the subsdcript value of phosphorus in formula I is about 0.5 to 1.75, of M about 0.8 to 2, of copper about 0.1 to 0.8, of vanadium about 0.1 to 0.8 and of X about 0.02 to 0.5.

9. The composition of claim 8 which is essentially 100% active.

10. The composition of claim 8 diluted with a support.

11. The composition of claim 10 where the support is a low surface area alumina.

12. The composition of claim 1 where X is lead.

13. The composition of claim 1 where X is barium.

14. The composition of claim 13 where Y is germanium.

* * * * *